United States Patent [19]

Sato

[11] Patent Number: 4,907,191

[45] Date of Patent: Mar. 6, 1990

[54] DATA PROCESSING APPARATUS AND DATA PROCESSING METHOD

[75] Inventor: Akihiko Sato, Tokyo, Japan

[73] Assignee: Kabushiki Kaisha Toshiba, Kawasaki, Japan

[21] Appl. No.: 180,845

[22] Filed: Apr. 12, 1988

[30] Foreign Application Priority Data

Apr. 13, 1987 [JP] Japan ................................. 62-88639

[51] Int. Cl.$^4$ ........................ G06F 15/06; G06F 15/42
[52] U.S. Cl. ................................. 364/900; 364/922; 364/962; 364/962.1; 364/400
[58] Field of Search ............... 364/178, 179, 181, 182, 364/188, 192, 551.01, 569, 200, 900, 554

[56] References Cited

U.S. PATENT DOCUMENTS

| | | | |
|---|---|---|---|
| 3,872,448 | 3/1975 | Mitchell, Jr. | 364/200 |
| 4,347,568 | 8/1982 | Giguere et al. | 364/900 |
| 4,360,125 | 11/1982 | Martindale et al. | 364/569 |
| 4,591,974 | 5/1986 | Dornbush et al. | 364/200 |
| 4,625,292 | 11/1986 | Philip | 364/569 |
| 4,715,002 | 12/1987 | Vernon et al. | 364/178 |
| 4,718,027 | 1/1988 | Richardson et al. | 364/554 |
| 4,805,089 | 2/1989 | Lane et al. | 364/188 |

Primary Examiner—Parshotam S. Lall
Assistant Examiner—Christopher L. Makay
Attorney, Agent, or Firm—Oblon, Spivak, McClelland, Maier & Neustadt

[57] ABSTRACT

A data processing method uses a file which has sequentially arranged records each having a data area for designating the number of measurements for each object or target to be measured, a data area provided for each of a plurality of pre-set measurement items, and a data area for storing data relating to the different times at which the items were measured. When measured data of each item are entered in the file, the time which has elapsed since the entry of the preceding measured data is determined. If the time is greater than a predetermined time, or if it is smaller than the predetermined time but the measured items are the same as the previously-measured items, then the data of the number of the preceding measurements is updated, the current measured data is stored in the data areas of the associated measurement items of the next record, and the data of the current measuring time is stored in the measuring time data area of that record. If the time which has elapsed is within the predetermined time and the measured items differ from the previous ones, the current measured data is stored in the data areas of the associated measurement items of the same record as used for recordintg the preceding measured data.

10 Claims, 12 Drawing Sheets

DATA PROCESSING APPARATUS AND DATA PROCESSING METHOD

Background of the Invention

1. Field of the Invention

The present invention relates to a handy terminal for use in accessing a computer to classify, maintain and manage various data, which should be manually acquired as in a case where no sensors are employed for automatic acquisition of the data, such as data which represents conditions of a patient in a ward which must be measured several times a day (e.g., body temperature, blood pressure, pulse or sphygmus, etc.), based on the types of data and the number of times the data items have been measured, and a data processing method executed by the handy terminal.

2. Description of the Related Art

The prior art will be explained below with reference to data management of patients in a ward.

In a ward, a nurse usually checks the patients several times a day to measure their body temperature, blood pressure, pulse, respiration number and the like, and records the data on a check sheet. These data are manually classified and written on a sheet called a temperature chart for each patient.

Since the number of measuring items, the number of times each item is measured and the like differ for each patient, it can become very troublesome to write the data on the temperature charts for each patient. Further, in various industries, it is often necessary to manually acquire and manage data, like patient data, whereas no sensors can be used in the acquisition of the data, thus requiring a troublesome manual data management.

SUMMARY OF THE INVENTION

Accordingly, it is an object of this invention to provide a data processing apparatus which can edit data, if input in a disorderly manner, based on the input time and the items which were measured, and maintain the data in a format which facilitates the preparation of the necessary charts, graphs and the like at a later time.

A data processing method employed by the data processing apparatus of this invention uses a file which has sequentially arranged records each having a data area for designating the number of measurements for each object or target to be measured, a data area provided for each of a plurality of pre-set measurement items (categories), and a data area for storing data relating to the times at which the data items were measured. When measured data of each item are entered in the file, the time which has elapsed since the preceding measured data entry is determined. If the time is greater than a predetermined time, or if it is smaller than a predetermined time but the measured items are the same as the previously-measured items, then the data of the number of the preceding measurements is updated, the current measured data is stored in the data areas of the associated measurement items of the next record, and the data representing the time at which the current data items were measured is stored in the measuring time data area of that record. If the time which has elapsed is within the predetermined time and the measured items differ from the previous ones, the current measured data is stored in the data areas of the associated measurement items of the same record as used for recording the preceding measured data.

According to this invention, a data entry interval is discriminated from the time at which the measured data is entered, and if the interval is found to be greater than a predetermined time, the entered data is considered to be the next measured data, the number of times the data has been measured is updated and the current measured data and the current data representing the time at which the data is measured are stored in the next record. If the data entry interval is within the predetermined time and the measurement items are the same as the previous ones, the entered data is considered to be the next measured data and the measured data is stored in the above manner. If the data entry interval is within the predetermined time with the current measurement items differing from the previous one, the entered data is not considered to be the next measured data, so that the number of times the data has been measured is not updated and the currently measured data is stored in the same record as used for recording the previous measured data.

DETAILED DESCRIPTION OF THE PREFERRED EMBODIMENTS

An embodiment of this invention will be explained below referring to the accompanying drawings.

Figure 2A:
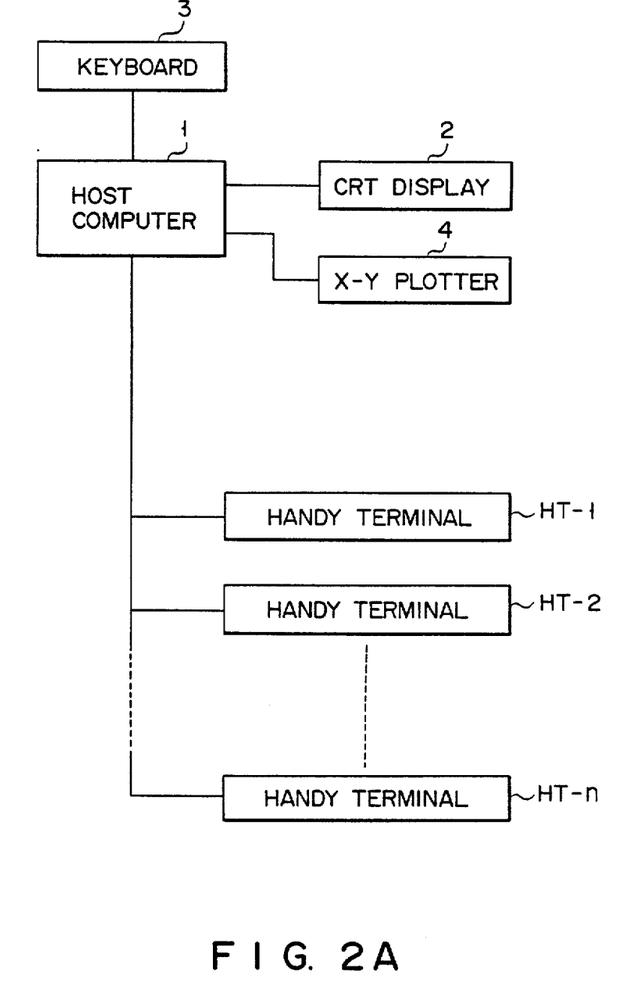
FIG. 2A is a block diagram illustrating a data processing system, which includes a plurality of handy terminals for executing the data processing of FIG. 1, and a host computer linked to the handy terminals to edit data therefrom.

In FIG. 2A, HT-1 to HT-n are handy terminals (hereinafter simply referred to as HT). Measured data is manually entered. The present system includes a plurality of handy terminals HT-1 to HT-n and data may be entered through any HT. The acquired data is all transferred to host computer 1 by linking the associated HT to computer 1 and the HT is initialized when host computer 1 acknowledges the data reception. Host computer 1, upon receipt of the measured data, classifies and files the data based on the measurement items and the times at which the data were measured. Upon request made through keyboard 3, host computer 1 can display the filed measured data, as maintenance data, on CRT display 2 in an easily legible form or can prepare graphs and charts of the filed measured data through X-Y plotter 4.

Figure 2B:
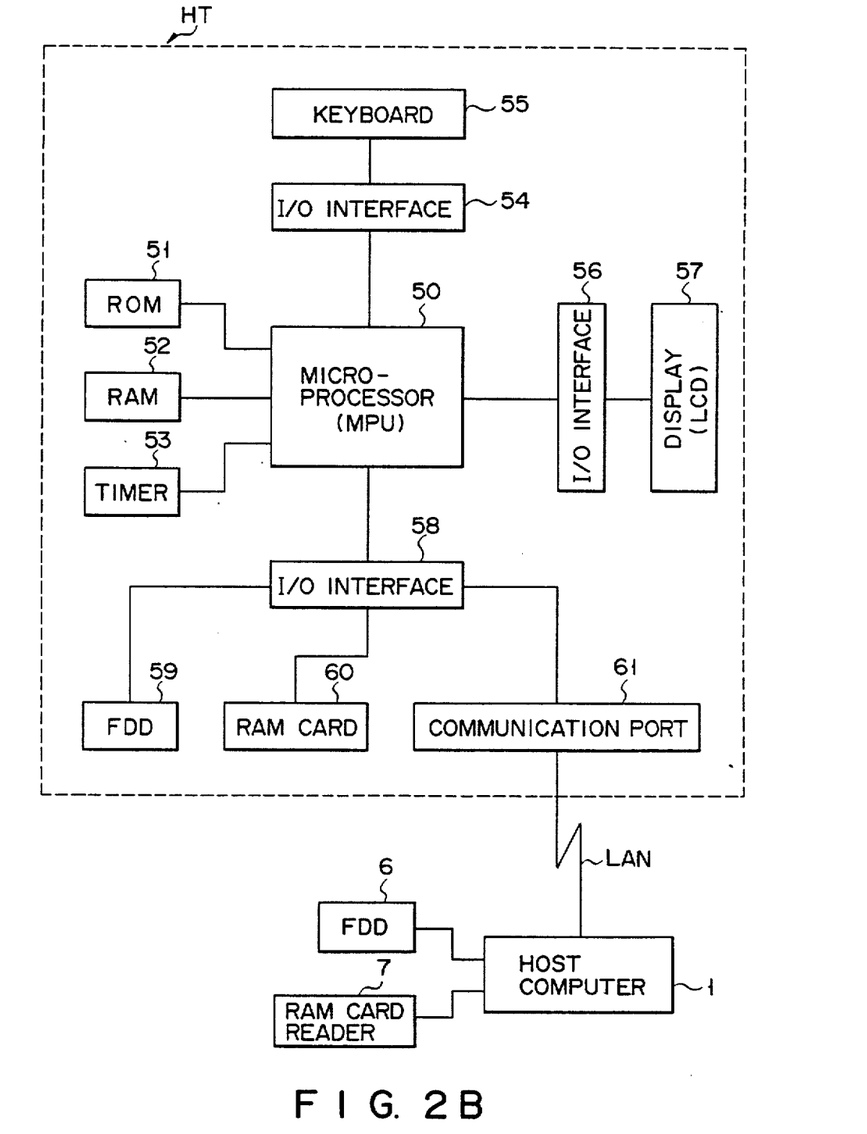
FIG. 2B is a block diagram illustrating the internal arrangement of each handy terminal shown in FIG. 2A.

FIG. 2B illustrates the internal arrangement of each handy terminal HT (HT-1 to HT-n) shown in FIG. 2A.

Terminal HT comprises, for example, 8-bit CMOS microprocessor 50 (hereinafter referred to as MPU) and peripheral devices 51 to 61. The operating system of MPU 50 and the other system programs are stored in ROM 51 in advance. RAM 52 stores data to be processed by MPU 50. MPU 50 is coupled to timer 53 which also serves as a clock generator to generate its operational clocks, and uses this timer 53 to record the time at which data is entered.

The data input to MPU 50 is entered through I/O interface 54 by means of keyboard 55. The entered data or data processed in MPU 50 is displayed through I/O interface 56 on display 57, which may be a liquid crystal display type panel.

The data entered in or processed in MPU 50 is transferred through I/O interface 58 to microfloppy drive 59, for example, of a 3.5 inch size or RAM card writer 60 (which can be an IC card writer, a magnetic card writer, etc.) to be recorded on a floppy disk or a RAM card. The recorded data is later read out by floppy drive 6 or RAM card reader 7 of host computer 1 and stored in a memory bank within the computer 1.

The individual handy terminals HT may be coupled through serial communication port 61 to host computer 1 to build a local area network (LAN).

Figure 3:
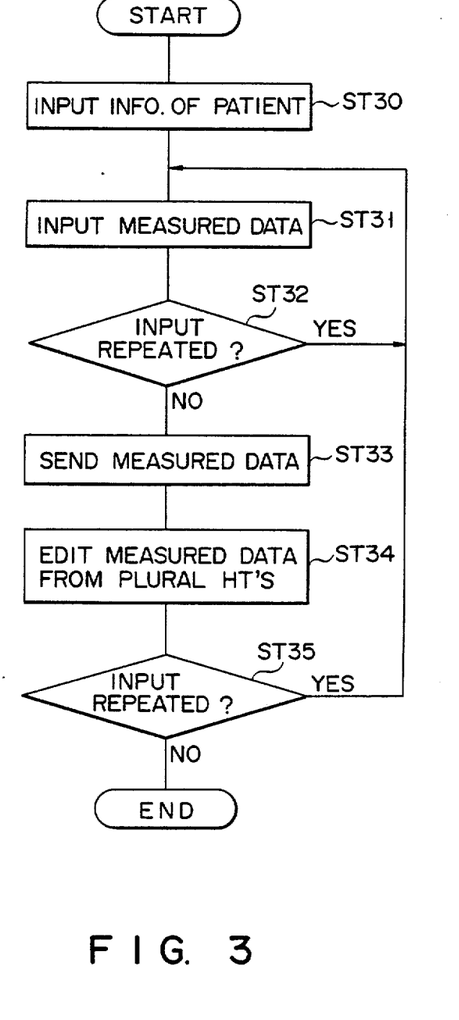
FIG. 3 is a flowchart illustrating the operational sequence of the data processing system shown in FIG. 2A.

FIG. 3 illustrates the operational sequence of a ward control system embodying this invention. Information about the patients is transferred in advance to the individual handy terminals from host computer 1, which may be located in a nurse station (step ST30).

A nurse makes the round of his/her assigned block and enters the data representing the physical conditions of the patients into his/her own HT (step ST31; YES in step ST32). Upon entering the necessary data (NO in step ST32), the nurse transmits the acquired data to host computer 1 through a communication line (LAN) (step ST33); the data transmission can be executed at a desired timing. Upon reception of the data, host computer 1 sends a data clear command to the HT. Editing steps (ST34 and ST35) in FIG. 3 will be described later.

Figure 4:
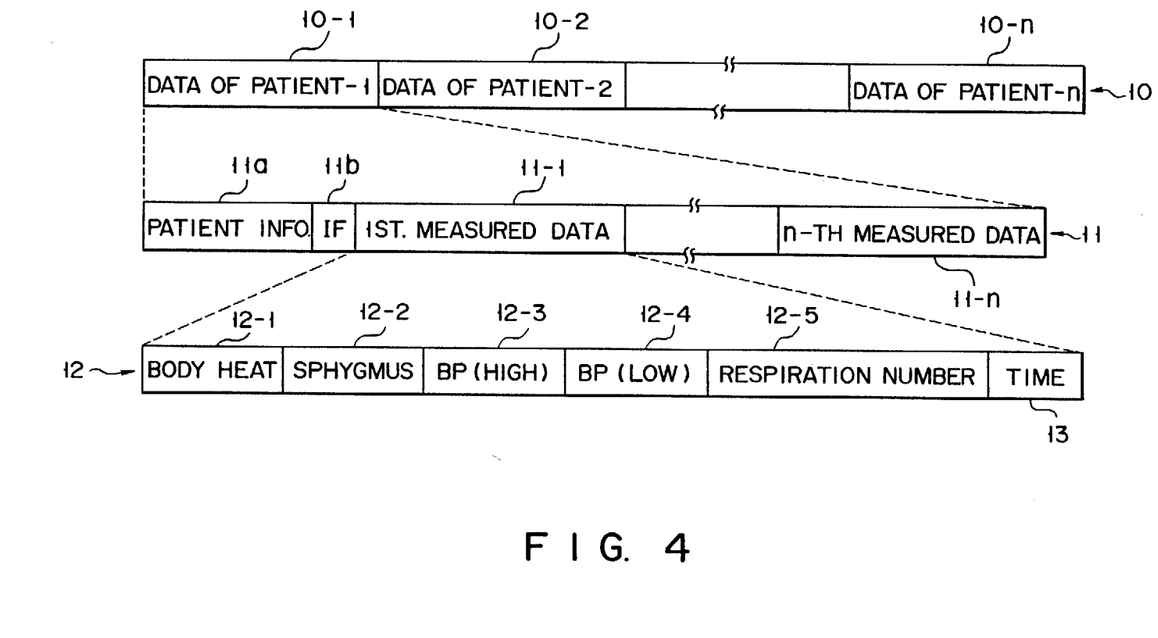
FIG. 4 is a diagram exemplifying the file structure for data processed by each handy terminal shown in FIG. 2A.

FIG. 4 illustrates the file structure used in the HT. In the figure, numeral 10 designates the entire structure of the file, numeral 11 represents a detailed file structure of one patient, and numeral 12 designates a detailed file structure for a single measuring of data for one patient.

Figure 1:
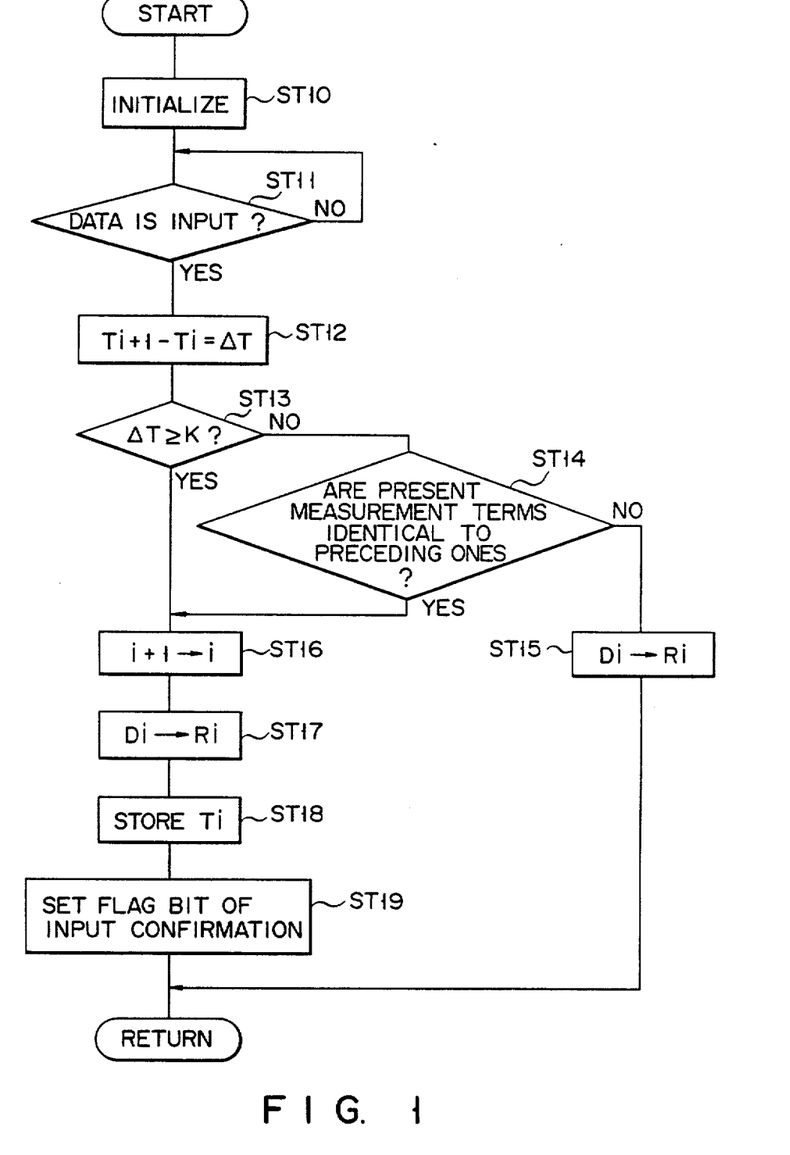
FIG. 1 is a flowchart illustrating the sequence of the data processing applied to a handy terminal according to one embodiment of this invention.

The data for each item measured is edited in the HT as shown in FIG. 1. Upon reception of the data clear command from host computer 1, each HT initializes an input confirmation flag to be described later (step ST10 in FIG. 1). After the aforementioned initialization process, data entry is then permitted. In this example, the nurse is to measure 5 data items for each patient (body temperature, sphygmus, blood pressure (high), blood pressure (low), and respiration). The number of data items to be acquired in a single measurement can be arbitrarily set within the range between one to five for individual patients, and the number of measurements per day can also range between one to seven depending on the patient. In this example, the time interval between the i-th measurement and the (i+1)-th measurement for one patient is set to be equal to or greater than K hours.

FIGS. 5A-5D illustrate the status of the file within the HT when the (i+1)-th measurement for patient A is carried out, provided that the measured data of patient A up to the i-th measurement has been entered.

Figure 5A:
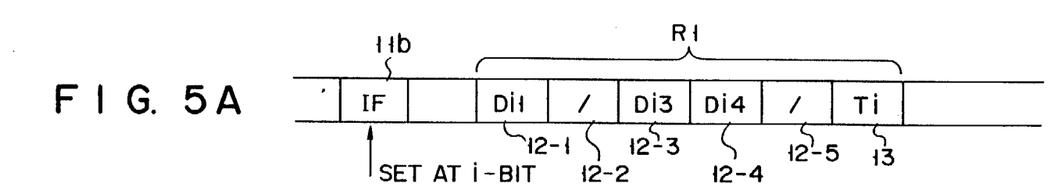
FIGS. 5A to 5D are detailed diagrams of the file structure shown in FIG. 4.

FIG. 5A illustrates the file status prior to the (i+1)-th measurement; $D_{i1}$, $D_{i3}$, and $D_{i4}$ in record $R_1$ indicate the data of the previous measurements stored in measurement item data areas (12-1, 12-3, and 12-4 in FIG. 4), and "/" indicates that there is no data in the marked measurement item data areas (12-2 and 12-5).

The input confirmation flag IF (11b) representing the number of measurements is set at the i-th bit. $T_i$ represents the time at which the previous measuring occurred.

The following explains the status of the file after the (i+1)-th data has been entered for the different cases.

CASE 1

Figure 5B:
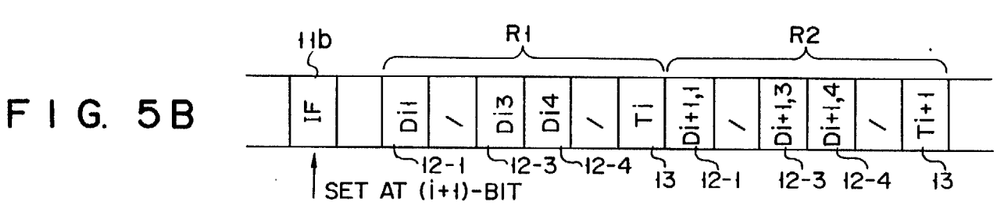

As shown in FIG. 5B, measured data $D_{i+1,1}$, $D_{i+1,3}$, and $D_{i+1,4}$ for the same items as the previous measured data (12-1, 12-3, and 12-4) are entered (YES in step ST11 in FIG. 1). In this case, irrespective of whether $T_{i+1}-T_i$ is greater or smaller than K hours, the (i+1)-th measurement is assumed to have been carried out (YES in step ST13 or ST14), the input confirmation flag (11b) is set at the (i+1)-th bit (updating of the number of measurements) (step ST16). Then, measured data $D_{i+1,1}$, $D_{i+1,3}$, and $D_{i+1,4}$, and time data $T_{i+1}$, are stored in the associated data areas (12-1, 12-3, 12-4) of next record $R_2$ (step ST17). The data processing in this case is executed in the sequence of steps ST13, ST14, and ST16-ST19 in FIG. 1.

CASE 2

Figure 5C:
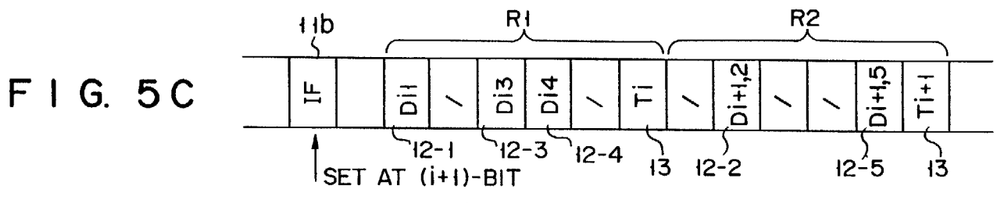

In this case, as shown in FIG. 5C, either of measured data $D_{i+1,2}$ and $D_{i+1,5}$ of different items (12-2, 12-5) than the previously-measured items (12-1, 12-3, 12-4) is entered; $D_{i+1,1}$, $D_{i+1,3}$, and $D_{i+1,4}$ of the same items as the previously-measured items are not entered; and time difference $\Delta T$ between previous measuring time $T_i$ and current measuring time $T_{i+1}$ is $(T_{i+1}-T_i) \geq K$ (YES in ST13). In this case, the (i+1)-th measurement is determined to have been carried out, and measured data $D_{i+1,2}$ and $D_{i+1,5}$ and time data $T_{i+1}$ are stored in their respective data areas (12-2, 12-5, 13) of next ((i+1)-th) record $R_2$. The input confirmation flag (11b) is set at the (i+1)-th bit. The data processing in this case is executed in the sequence of steps ST13 and ST16-ST19 in FIG. 1.

CASE 3

Figure 5D:
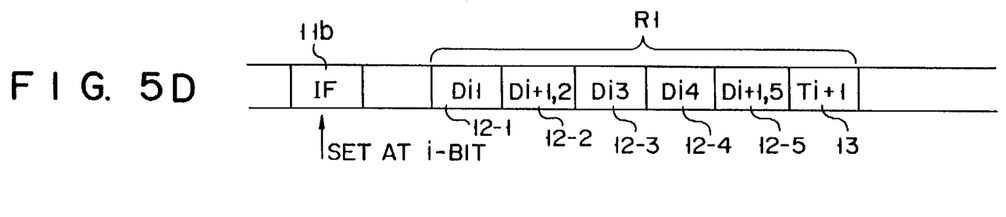

This is the case in which, as shown in FIG. 5D, either of measured data $D_{i+1,2}$ and $D_{i+1,5}$ of different items (12-2, 12-5) than the previously-measured items (12-1, 12-3, 12-4) is entered; $D_{i+1,1}$, $D_{i+1,3}$ and $D_{i+1,4}$ of the same items as the previously-measured items are not entered; and time difference $\Delta T$ attained in step ST12 is $(T_{i+1}-T_i)<K$ (NO in step ST13). In this case, the current measurement is determined to be the i-th one and measured data $D_{i+1,2}$ and $D_{i+1,5}$ are stored in their respective data areas (12-2, 12-5, 13) of record $R_1$ used for the i-th measurement (step ST15). The input confirmation flag remains set at the i-th bit (no updating of the number of measurements). The data processing in this case is executed in the sequence of steps ST13, ST14, and ST15 in FIG. 1.

Based on the items of the measured data or the different times at which the items were measured, the measured data can be sequentially managed.

Then, individual handy terminals HT-1 to HT-n, in which various data have been collected in the above manner, are coupled through a transmission line to host computer 1, so that the collected data is sent to host computer 1 (step ST33 in FIG. 3).

Figure 6:
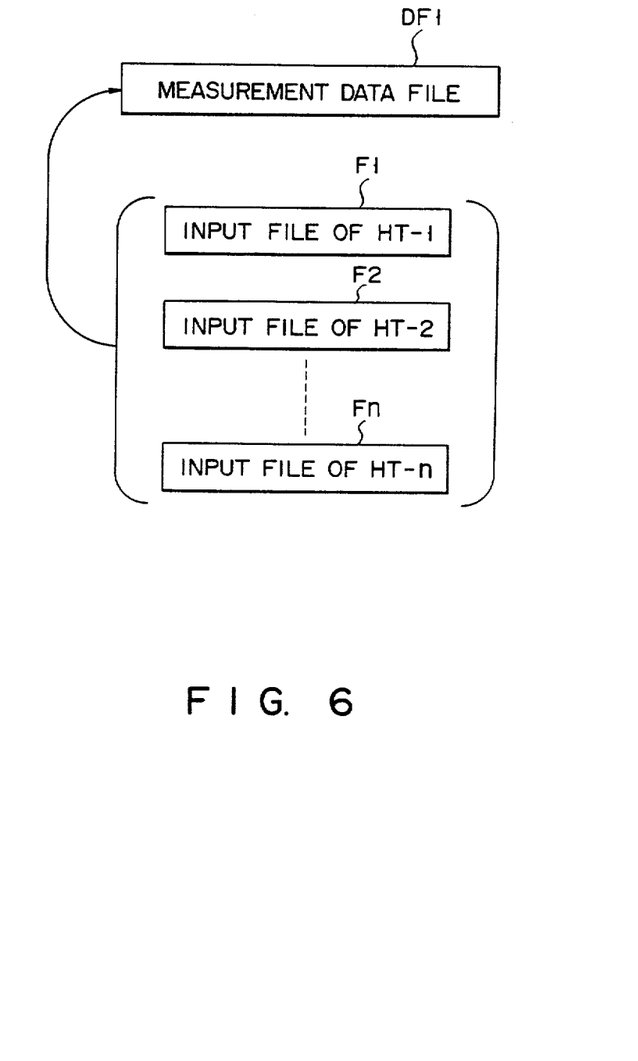
FIG. 6 is a diagram for explaining the flow of data from each handy terminal, shown in FIG. 2A, to the host computer.

Host computer 1 edits the measured data transferred from a plurality of handy terminals to provide a single file. That is, as shown in FIG. 6, the data of input files F1-Fn of a plurality of handy terminals HT-1 to HT-n are edited to provide measured data file DF1 of host computer 1 (step ST34 in FIG. 3).

An example of the editing process will be explained below.

Figures 7A, 7B:
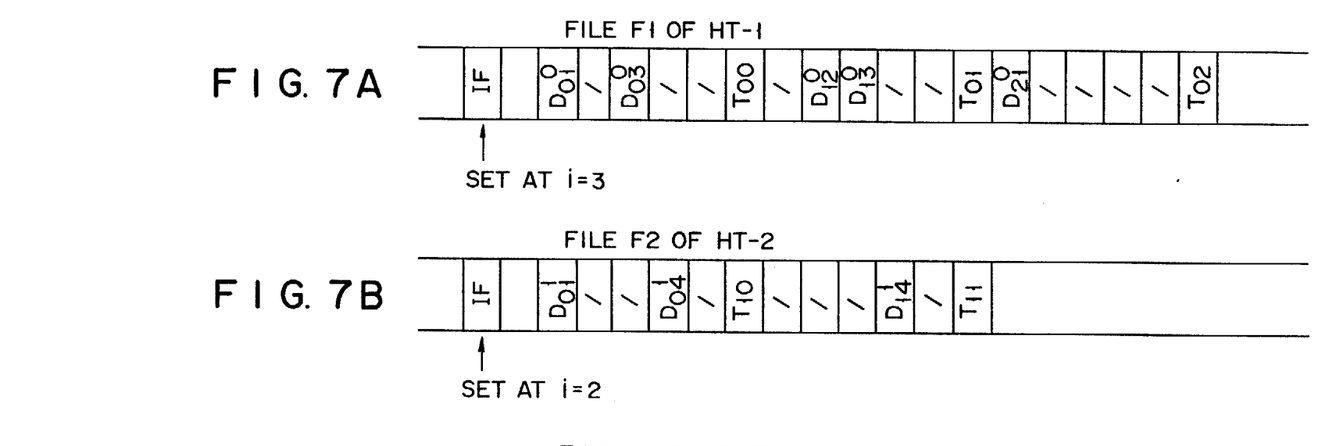
FIGS. 7A to 7C are detailed diagrams exemplifying the file structures, as shown in FIG. 6, in the individual handy terminals.
Figure 7C:
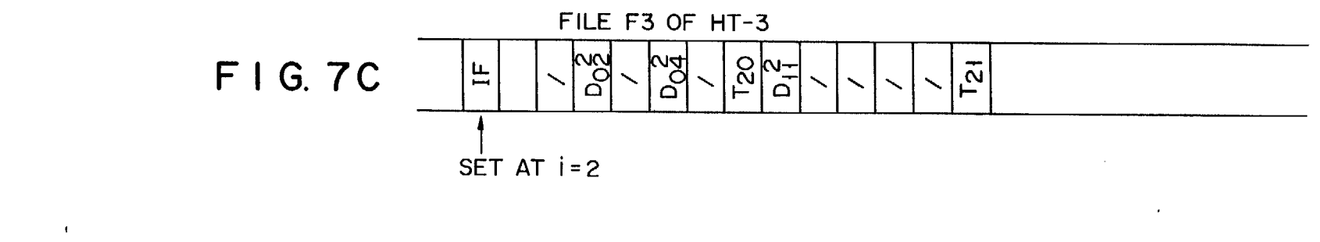
Figure 8A:
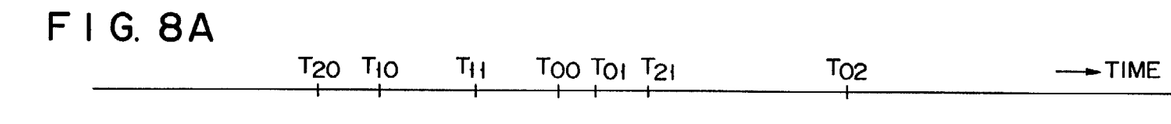
FIGS. 8A to 8D are detailed diagrams exemplifying the file structures used when the data in the file shown in FIG. 7 is edited by the host computer.
Figure 8B:
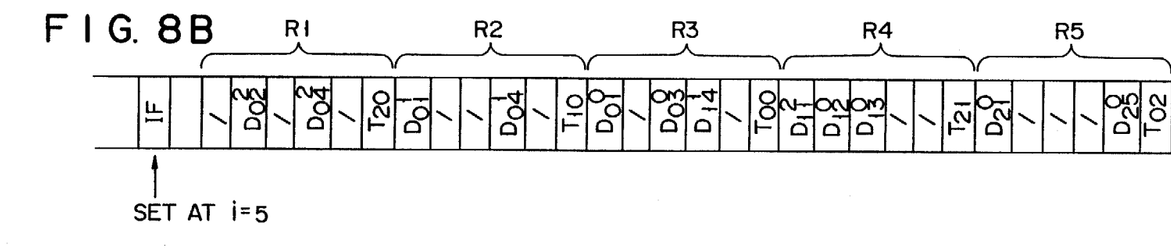
Figure 8C:
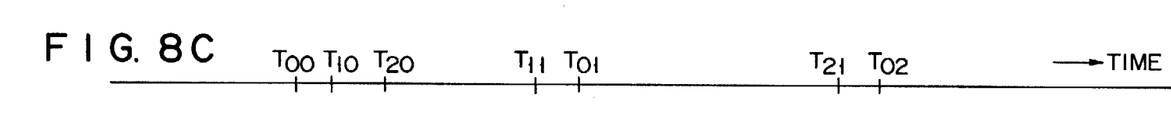
Figure 8D:
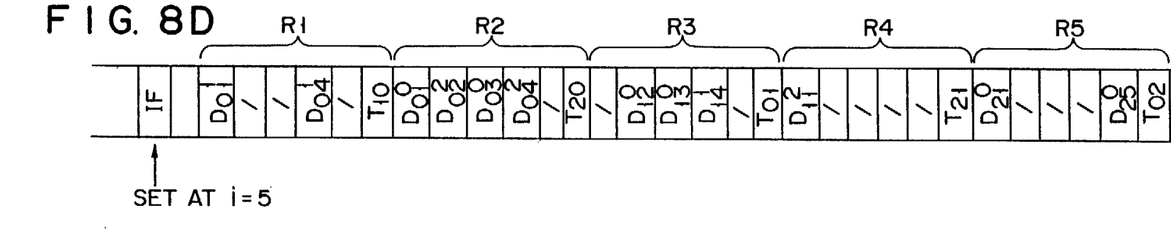

If the data of input files F1-Fn of individual terminals HT-1 to HT-3 are as shown in FIGS. 7A-7C, the measured data, after editing has taken place, becomes as shown in FIG. 8B or 8D.

In FIGS. 7A-7C, it is assumed that terminals HT-1, HT-2, and HT-3 are respectively initiated in three measurements, two measurements and two measurements. $T_{ni}$ represents the measuring time, $D_{ij}^n$ represents the data for each measured item, and "/" indicates that no data has been input which corresponds to the designated data item areas, where n corresponds to the one-decremented number of handy terminal HT, i represents the number of measurements, and j, the data item number (j=1 to 5 in the case of FIG. 4).

The measured data is edited on the basis of time $T_{ni}$ and measurement items (12-1 to 12-5 in FIG. 4) as the data processing described earlier with reference to FIG. 1. As a result, the data file in host computer 1 becomes the one shown in FIG. 8B or 8D.

FIG. 8A illustrates the relationship between the different times at which the data items were measured with respect to HT-1 to HT-3, and FIG. 8B illustrates the file structure after completing the editing of the measured data acquired in this case. FIG. 8C illustrates another relationship between the different times at which the data items were measured with respect to HT-1 to HT-3, and FIG. 8D illustrates the file structure after the editing of the measured data acquired in this case has taken place.

The file structures shown in FIGS. 7 and 8 are associated with the same patient. Generally, two to three HTs (three in this example) are provided in a ward, and a nurse uses any available one of the three HTs to enter the measured data of patients. Therefore, the measured data of one patient is often stored in different HTs; in this example, such data is distributed over three handy terminals HT-1 to HT-3. In this respect, all of HT-1 to HT-3 are finally coupled to host computer 1 which in turn edits the transferred data to make a single file.

In the embodiment of FIG. 1, the predetermined time K which is used for discriminating time difference ΔT between the previous measurement and the current measurement is set to be one hour.

The following explains the case as shown in FIGS. 8A and 8B. In FIG. 8A, the first measurement is carried out with HT-3 (n=2) at time $T_{20}$, measured data $D_0^2{}_2$ and $D_0^2{}_4$ and time data $T_{20}$, are stored in record $R_1$, and the input confirmation flag is set at the first bit (i=1).

The next measurement is carried out with HT-2 (n=1) at time $T_{10}$, and the time which has elapsed since the first measurement falls within one hour, i.e., $(T_{10}-T_{20})<K$. Since the current measurement includes the same measurement item $(D_{04})$ as the previous measurement, the measured data $D_0^0{}_1$ and $D_0^1{}_4$ and time data $T_{10}$ are stored in the next record $R_2$, and the input confirmation flag is set at the second bit (i=2). (The number of measurements i is updated to i+1.)

The next measurement is carried out with HT-2 (n=1) at time $T_{11}$, and the time relationship between the current measurement and the previous measurement is $(T_{11}-T_{10})<K$. Since the current measurement includes the same measurement item as the previous measurement, the measured data $D_1^1{}_4$ is stored in the next record $R_3$, and the input confirmation flag is set at the third bit (i=3).

The next measurement is carried out with HT-1 (n=0) at time $T_{00}$. In this case, since the time relationship between the current and previous measurements is $(T_{00}-T_{11})<K$, and the current measurement includes different items from those of the previous measurement, the measured data $D_0^0{}_1$ and $D_0^0{}_3$ are stored in the same record $R_3$ as used for the previous measurement. The input confirmation flag remains set at the third bit (i=3).

With regard to the time data, the latter time data $T_{00}$ is stored. (Although, previous time data $T_{11}$ may instead be stored.) Similarly, data measured at times $T_{01}$ and $T_{21}$ are stored together in record $R_4$. Since the time relationship between the current measurement at time $T_{02}$ and the previous measurement is $(T_{02}-T_{21})>K$, the measured data is stored in record $R_5$. In this case, the input confirmation flag is set at the fifth bit (i=5).

In the case shown in FIGS. 8C and 8D, the measured data is edited on the basis of the measuring times and the measurement items to make a single file in the same manner as in the above explained case.

With the above file structure, data which relates to the physical condition of each patient can easily be plotted on a graph or a table using CRT 2, X-Y plotter 4, or the like, shown in FIG. 2A.

Figure 9:
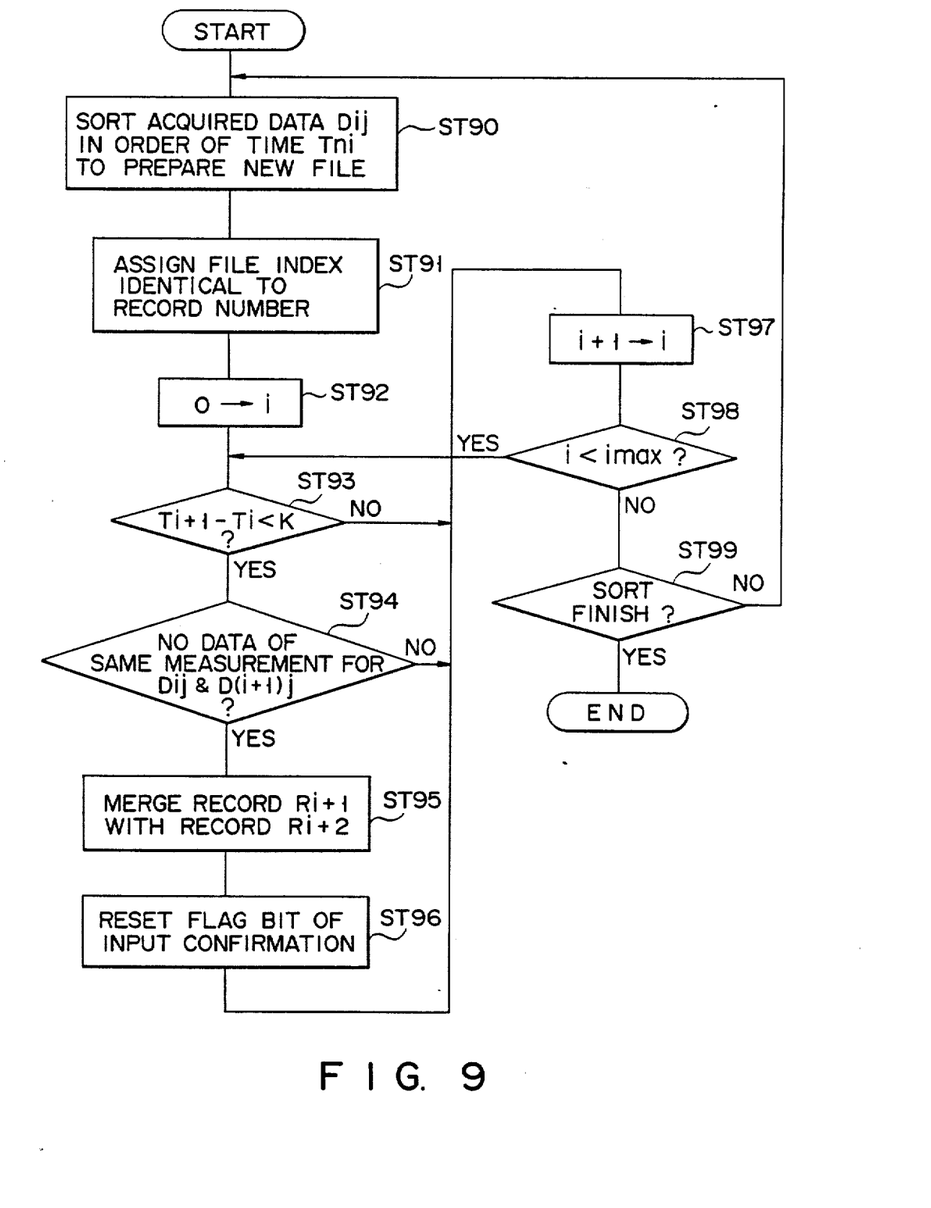
FIG. 9 is a flowchart illustrating the data editing sequence executed by the host computer shown in FIG. 2A.

FIG. 9 is a flowchart illustrating the data editing procedures performed by the host computer as shown in FIG. 2A. FIGS. 10A-10E illustrate examples of the file structure which is attained after the data has been edited by the host computer as shown in FIG. 2A. In these examples, $T_{ni}$ indicates the i-th measuring time of the (n-1)-th HT, $D_{ij}$ indicates the data of the j-th item acquired by the i-th measurement, and K indicates a predetermined time (e.g., one hour). (In this example, the maximum value [imax] of i is 6, and j varies between 1 to 5 according to the types of measured data 12-1 to 12-5.)

In FIG. 9, data $D_{ij}$ collected from the individual HTs are sorted by host computer 1 in accordance with measuring time $T_{ni}$ (FIG. 10A) to prepare a new file (FIG. 10B) (step ST90). Then, file indexes (0-6) corresponding to record numbers $R_1-R_7$ are assigned to the data $D_{ij}$ and measuring time data $T_{ni}$, so that a managed file (FIG. 10C) is prepared (step ST91).

Then, i is set to 0 (step ST92) and the time difference $(T_1-T_0)$ is compared with the predetermined time K (one hour) (step ST93). When this time difference is smaller than K (YES in step ST93), it is determined whether or not the previous measured data $D_{ij}$ and the current measured data $D_{(i+1)j}$ are associated with the same measurement items (step ST94). If the previous and the current measured data are not associated with the same measurement items (YES in step ST94), record $R_{i+1}$ is merged with record $R_{i+2}$ (step ST95), and the input confirmation flag (one bit) is reset (step ST96).

Then, i is incremented to i+1 (step ST97) and this incremented value is compared with its maximum value imax (=6) (step ST98). If the increment value i is smaller than 6 (NO in step ST98), the process returns to step ST93. If the increment value i is 6 (NO in step ST98), steps ST90 to ST98 are repeated with respect to measuring time $T_{ni}$ with the incremented of i. When the sorting operation of steps ST90-ST98 is completed (YES in step ST99), the editing operation preformed by host computer 1 is completed.

Figure 10A:
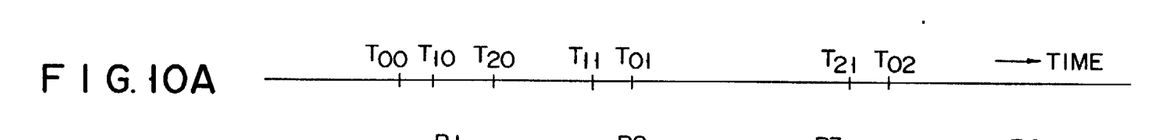
FIGS. 10A to 10E are diagrams exemplifying the file structures after the data has been edited by the host computer shown in FIG. 2A.
Figure 10B:
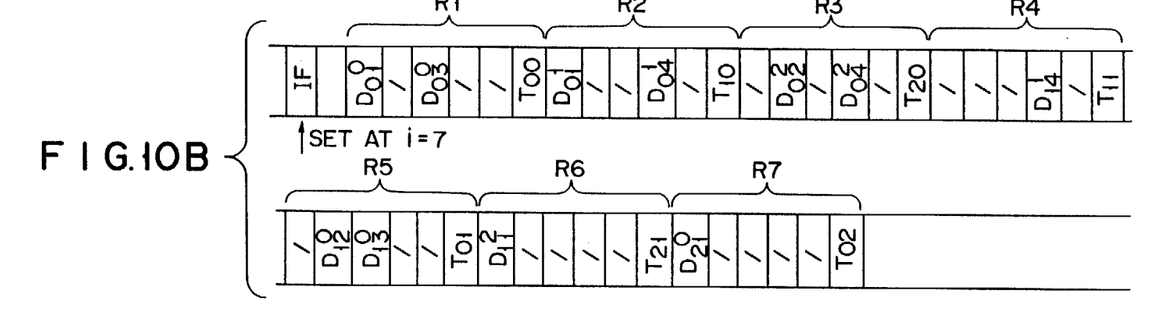
Figure 10C:
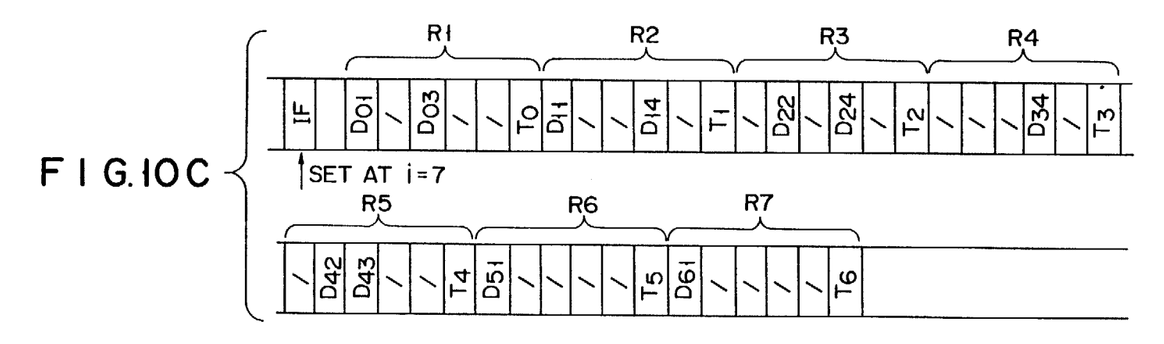
Figure 10D:
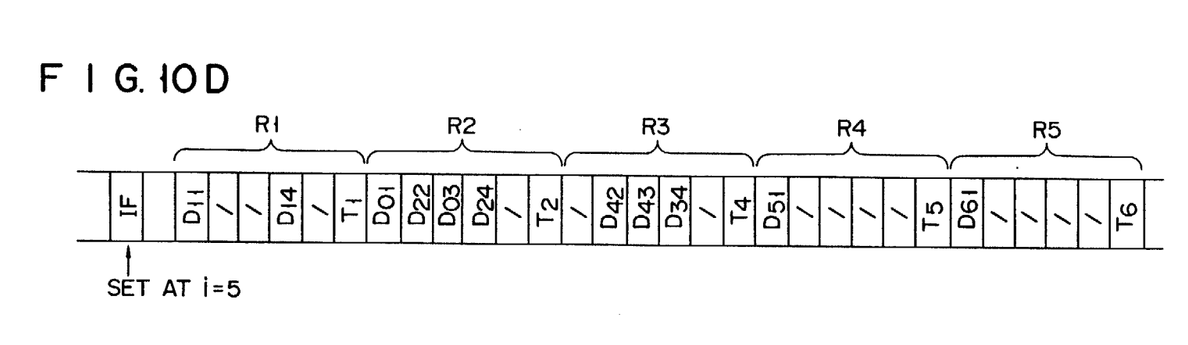
Figure 10E:
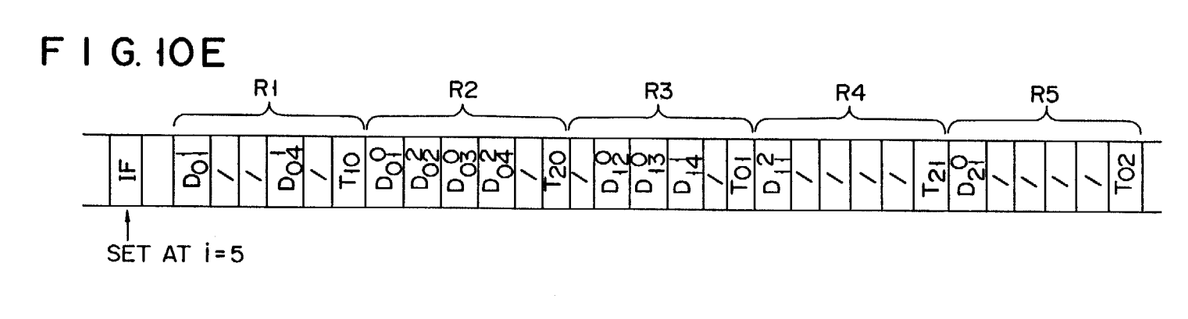

Provided that the file attained with respect to the time relationship shown in FIG. 10A is as shown in FIG. 10D, this file can be as illustrated in FIG. 10E when the form shown in FIG. 7 is used.

The following is a summary of the above operation. A nurse collects measured data using HTs, and couples the HTs to the host computer at a later time to transfer all the collected data to the host computer. The host computer classifies the collected data on the basis of the measurement items and measuring times, and provides a hard or soft copy corresponding to a temperature chart using the X-Y plotter or the like coupled to the computer. The data transferring work, which is to be manually performed according to a prior art systems, can be automatically executed using HTs and the host computer, so that data can easily be managed in a single file.

The above embodiment has been explained with reference to a control system in a ward; however, it can also be applied to data management in a plant, for example.

As has been explained above, according to this invention, data, even if entered in a disorderly manner, can be edited on the basis of the measurement items and measuring times in such a form as to easily provide tables and graphs at a later time.

What is claimed is:

1. A terminal for handling records each including, a number set area for setting a number of measurements, a data area provided for each of a predetermined number of categories, and a time area for recording a measuring time, said terminal comprising:
   computer means for managing said records;
   input means for inputting measured data for each of said categories into said computer means;
   timer means for informing said computer means of a time at which data input is performed through said input means,
   wherein said computer means has the following functions:
   (a) storing time data from said timer means into said time area;
   (b) storing measured data from said input means into said data areas;
   (c) detecting a time difference between preceding time data stored in said time area and current time data from said timer means, and comparing said detected time difference with a predetermined value;
   (d) detecting whether preceding categories stored in said data areas substantially match present categories from said input means;
   (e) updating measurement number data stored in said number set area, storing the measured data from said input means into said data areas of a record associated with said updated measurement number data, and storing said current time data from said timer means into said time area, when said time difference is greater than said predetermined value, or when said time difference is smaller than said predetermined value and said preceding categories stored in said data areas substantially match said present categories from said input means; and
   (f) leaving said measurement number data stored in said number set area to remain un-updated, and storing the measured data from said input means into said data areas of a record associated with measurement number data prior to updating, when said time difference is smaller than said predetermined value and said categories stored in said data areas differ from said present categories from said input means.

2. The terminal according to claim 1, wherein said terminal is formed to be a portable terminal and has a recording medium for recording a record for each of said targets to be measured.

3. A data processing system to which one terminal as claimed in claim 1 or more are coupled, said system comprising:
   host computer means for collecting said records from each of said terminals, and editing measured data with respect to each of said categories in each of said collected records for data classification and management.

4. The data processing system according to claim 3, wherein each of said terminals is formed to be a portable terminal which is detachable from said host computer means and has a recording medium for recording a record for each of said targets to be measured; and
   wherein said host computer means has means for reading data from said recording medium.

5. The data processing system according to claim 3, wherein each of said terminals is detached from said host computer means and disposed in an area which is close to each of said targets to be measured, and has communication means for sending said records for each of said targets to be measured to said host computer means.

6. A data processing method for handling records each including, a number set area for setting a number of measurements, a data area provided for each of a predetermined number of categories, and a time area for recording a measuring time, said method comprising the steps of:
   (a) storing time data into said time area;
   (b) storing measured data into said data areas;
   (c) detecting a time difference between preceding time data stored in said time area and current time data, and comparing said detected time difference with a predetermined value;
   (d) detecting whether preceding categories stored in said data areas substantially match present categories initiated in a present measurement;
   (e) updating measurement number data stored in said number set area, storing said measured data into said data areas of a record associated with said updated measurement number data, and storing said present time data into said time area, when said time difference is greater than said predetermined value, or when said time difference is smaller than said predetermined value and said preceding categories stored in said data areas substantially match said present categories; and
   (f) leaving said measurement number data stored in said number set area to remain un-updated, and storing the measured data into said data areas of a record associated with measurement number data prior to updating, when said time difference is smaller than said predetermined value and said categories stored in said data areas differ from said present categories.

7. The data processing method according to claim 6, wherein said method is executed by a portable terminal.

8. The data processing method according to claim 6, wherein said method is individually executed by one or more portable terminals, and a method to be executed by a data processing system to which said portable terminals are coupled, comprises the step of:

collecting said records from said portable terminals, and editing measured data with respect to each of said categories in each of said collected records for data classification and management.

9. The data processing apparatus according to claim 8, wherein each of said portable terminals has a recording medium for recording a record for an entity to be measured; and wherein the method to be executed by said data processing system further comprises the step of:

reading data from said recording medium.

10. The data processing method according to claim 8, wherein each of said portable terminals, is disposed in an area which is close to said entity to be measured; and wherein said data processing method to be individually executed by said portable terminals, further comprises the step of:

transmitting said records for each of said entity to be measured to said data processing system.

* * * * *